United States Patent [19]
Wada et al.

[11] Patent Number: 4,922,911
[45] Date of Patent: May 8, 1990

[54] ELECTRODE

[75] Inventors: Shintaro Wada; Yoichi Nomura; Hisanori Takahashi; Masayuki Konno, all of Osaka, Japan

[73] Assignee: Nitto Denko Corporation, Osaka, Japan

[21] Appl. No.: 333,833

[22] Filed: Apr. 5, 1989

Related U.S. Application Data

[63] Continuation of Ser. No. 95,189, Sep. 11, 1987, abandoned.

[30] Foreign Application Priority Data

Dec. 24, 1986 [JP] Japan .............................. 61-201177[U]

[51] Int. Cl.⁵ ................................................ A61B 5/04
[52] U.S. Cl. ...................................... 128/640; 128/798
[58] Field of Search ............... 128/639, 640, 798, 802, 128/803

[56] References Cited

U.S. PATENT DOCUMENTS

| | | |
|---|---|---|
| 4,172,745 | 10/1979 | Van Manen . |
| 4,393,584 | 7/1983 | Bare et al. . |
| 4,522,211 | 6/1985 | Bare et al. ............................ 128/640 |
| 4,657,023 | 4/1987 | Kuhn .................................... 128/640 |
| 4,679,563 | 7/1987 | Wada et al. ......................... 128/640 |
| 4,694,835 | 9/1987 | Strand ................................. 128/640 |

FOREIGN PATENT DOCUMENTS 0181057 5/1986 European Pat. Off. .
2345981 10/1977 France .

Primary Examiner—Lee S. Cohen
Attorney, Agent, or Firm—Sughrue, Mion, Zinn, Macpeak & Seas

[57] ABSTRACT

An electrode is disclosed, comprising an electrically conductive substrate and a shrinkable layer laminated on the substrate, wherein a cut is provided on the electrode so as to form a connection terminal portion projecting outwards upon shrinkage of the shrinkable layer.

6 Claims, 2 Drawing Sheets

ELECTRODE

This is a continuation of application Ser. No. 095,189, filed Sept. 11, 1987, now abandoned.

FIELD OF THE INVENTION

The present invention relates to an electrode which is suitable for use as, for example, an electrode for medical attention, or a connector to remove static electricity on a material to be bonded or to electrically connect materials to be bonded.

BACKGROUND OF THE INVENTION

As an electrode to be attached or fixed to the skin surface of a patient to transmit an electric signal from the skin surface of the living body to a medical or diagnostic equipment, or a connector to remove static electricity on the surface of a material to be bonded or to electrically connect materials to be bonded, an electrode with a terminal portion which is provided with a clip, a hook or a connector terminal for insertion of a pin has been proposed.

In the above electrode, however, the main body and a connector terminal are formed separately. Thus, the number of parts is increased, the administration becomes complicated, and the number of steps in production is increased. Production costs result in an increase.

Particularly when such electrode is used as an electrode for medical attention, various problems arise. For example, since the electrode comprises the main body and a connector terminal provided to the edge portion of the main body, when the connector terminal is erected and connected to the terminal of the medical or diagnostic equipment, the electrode bonded to the skin is raised at the point of the connector terminal and peeled off, resulting in the generation of stress by the force between the connector terminal portion and the skin surface. Since the connector terminal portion is peeled off, the attachment of the electrode becomes insufficiently low, and the stability of electric signal is lost. This phenomenon cannot be neglected when the electrode is used in the long term monitoring.

In order to overcome the such problems of the above electrode, applicant proposed the electrode wherein the electrode plate has a cut therein which provides a tongue to be connected to a clip etc. for a connector terminal portion as disclosed in the U.S. Pat. No. 4,679,563.

In this electrode, the tongue must be raised at use. However, the tongue cannot be easily raised and the such work becomes complicated since the tongue is provided in the electrode plate so as to be in the same level as that of the electrode plate.

Therefore, the improvement of the such electrode has been desired.

SUMMARY OF THE INVENTION

As a result of extensive investigations to overcome the problems in the prior art, it has been found that a cut is provided in an electrode so that upon irradiation of heat or radiation on the cut portion, the cut portion shrinks and projects outwards, and the projected cut portion is used as a connector terminal to the terminal of the equipment to connect, such as an apparatus for medical attendance or diagnosis.

Accordingly, an object of the present invention is to provide an electrode which can overcome the prior art problems. The electrode according to the present invention comprises an electrically conductive substrate and a shrinkable layer laminated on the substrate, wherein a cut is provided on the electrode so as to form a connection terminal portion projecting outwards upon shrinkage of the shrinkable layer

BRIEF DESCRIPTION OF THE INVENTION

Figure 1:
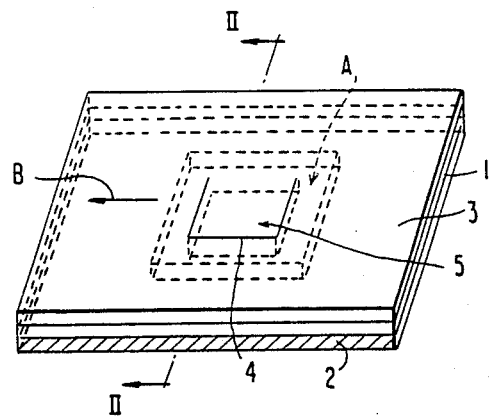
FIG. 1 is a perspective view of an electrode according to the present invention.

FIGS. 4 to 9 each is a plan view of other embodiments.

The reference numerals used are as follows:

(1) . . . Electrically conductive substrate, (2) . . . Electrically conductive adhesive layer, (3) . . . Shrinkable layer, (4) . . . Cut, (5) . . . Connection terminal portion, (6) . . . Non-adhesive liner layer, (A) . . . Non-contact area, (B) . . . Shrink direction, (C) . . . Direction of line connected to the base end.

DETAILED DESCRIPTION OF THE INVENTION

The electrically conductive substrate used in the present invention is preferably a flexible material. The substrate is not critical so long as it is an electrically conductive foil or sheet (film).

Preferred embodiments of such electrically conductive substrates are shown below.

(1) The electrically conductive substrate is a foil or sheet having a thickness of 10 to 500 $\mu$m which is made of platinum, gold, silver, copper, zinc, tin, aluminum, nickel, indium or alloys of combinations of the above metals, or alloys made mainly of the above metals, or stainless steel.

(2) The electrically conductive substrate is a laminated film comprising a metal foil and a reinforcing plastic film provided on one side of the metal foil. The metal foil is made of platinum, gold, silver, copper, zinc, tin, aluminum, nickel, indium, or alloys of the above metals, or alloys made mainly of the above metals, or stainless steel. The metal foil has a thickness of 10 $\mu$m or less.

The plastic film includes a film made of at least one synthetic resin selected from the group consisting of polyolefins such as polyethylene and polypropylene, polyesters such as polyethylene terephthalate, an ethylene-vinyl acetate copolymer, polyvinyl chloride, polyvinylidene chloride, polyvinyl formal, polytetrafluoroethylene, an acryl resin, polyurethane, polyamide and polyimide.

(3) The electrically conductive substrate is made of a plastic film, paper, woven or unwoven fabrics with a metal deposited layer, a non-electrolytic plated layer or a metal foil laminated thereon.

Examples of the plastic film which can be used in the present invention include films made of the synthetic resins listed in (2) above.

The paper, woven or unwoven fabrics which can be used in the present invention include those made of synthetic resins, cellulose, cotton cloth or the like.

The electrode according to the present invention has a structure comprising the electrically conductive substrate and the shrinkable layer laminated on one side of the substrate.

The shrinkable layer which can be used in the present invention is not critical so long as it shrinks in one direction upon irradiation of heat or radiation and makes the connection terminal portion as described hereinafter project outwards.

As the heat source, a hot air source, e.g., a drier, a heating iron, an infrared heater and so on can be used.

As the above irradiation, at least one of sun light, ultraviolet ray, electron ray, radiation and so on can be used.

The above heat shrinkable layer includes a sheet (film), a foam, or woven or unwoven fabrics which are made of polybutadiene, polyisoprene, chloroprene, polyester, polyvinyl chloride, polypropylene, polyethylene, ethylene-vinyl acetate copolymer, polyvinyl chloride, polyvinyl formal, polytetrafluoroethylene, an acryl resin, polyurethane, polyamide, polyimide or copolymers made mainly of the above monomers.

The shrinkable layer may be laminated by laminating the above sheet on the electrically conductive substrate or coating a paint of the above resin on the electrically conductive substrate.

As the layer which hardens or cross-links upon irradiation of radiation, thereby shrinking, those made of an acryl resin, polyester, polyurethane or acryl oligomer, polyester oligomer, polyurethane oligomer, or monomers thereof can be used. This layer is laminated on the electrically conductive substrate as in the case of the heat shrinkable layer.

In the electrode comprising the electrically conductive substrate with the shrinkable layer laminated thereon according to the present invention, a cut is provided so as to form a connection terminal portion which projects outwards upon shrinkage of the shrinkable layer.

The cut makes the portion shrink and project outwards in use, and the projected portion is connected to a terminal of the unit to be connected, e.g., an equipment for medical or diagnostic attention, as a connector terminal portion. In this sense, the structure is not critical so long as it is such that the cut portion, i.e., the connection terminal portion, shrinks, thereby projecting outwards.

In more detail, the cut may be formed in any desired form such as in the nearly U-shaped form, or the nearly V-shaped form, thereby forming the connection terminal portion. The cut may be formed in the form of hook to form the connection terminal portion. Furthermore, two lines may be cut in parallel with each other with a suitable clearance between them from the end of the shrinkable layer.

In the present invention, if the direction of a line connecting the base end of the cut in the above connection terminal portion is formed so as to form an angle of 0° to 60° relative to the direction of shrinkage of the shrinkable layer, there can be obtained an advantage that even if the weight of the terminal (e.g., a clip) or any load is applied when or after the cut portion, i.e., the connection terminal portion, is connected to the terminal (e.g., a clip) of the medical or diagnostic equipment, the break-down from the base end of the cut in the connection terminal portion can be prevented efficiently.

So long as the cut portion in the shrinkable layer, i.e., the strength of the connection terminal portion, is sufficiently high, the direction in which the connection terminal portion is formed is not critical. However, it is preferred to provide the cut in the manner as described above because even if an unexpected great tearing force is applied during the handling such as connection to the equipment, no breakdown occurs and as a result, the handling becomes easy.

In a case where the shrinkable layer is formed by biaxial stretching, the above shrinkage direction means a direction in which the shrinkage ratio is higher.

In the present invention, an electrically conductive adhesive layer can be provided on the side of the electrically conductive substrate on which the shrinkable layer is not provided. It is preferred that the adhesive layer be provided on areas except the connection terminal portion of the electrically conductive substrate because if so, when the shrinkable layer is shrinked, the cut portion constituting the connection terminal portion can be easily projected outwards.

The above electrically conductive adhesive layer can be formed by using a mixture of a conductivity-imparting substance such as various metal powders, carbon powder or an aqueous solution of potassium chloride or sodium chloride (electrolyte), and an adhesive agent such as polysaccharides, semi-synthetic polymers such as various celluloses, or synthetic polymers such as polyacrylic acid and/or its salts, polyacrylic acid ester derivatives, polyvinyl alcohol or other hydrophilic polymers.

In forming the electrically conductive adhesive layer on the electrically conductive substrate, a non-adhesive liner layer such as polyester film may be provided between the electrically conductive substrate and the electrically conductive adhesive layer on areas corresponding to the desired portion.

The above non-adhesive liner layer is not critical. In particular, a foamed material in the compressed form can be used in order to easily erect the above connection terminal portion.

The electrode of the present invention has the structure as described above, and the cut portion rolls up easily, projecting outwards when the shrinkable layer is shrunk. In the case of a monoaxially stretched film in which the shrinkage is caused in the certain direction, it is preferred that the cut be provided in the direction in which the shrinkage occurs, because the outward projection is accelerated.

The projected portion can be electrically connected as a terminal portion to the terminal (e.g., a clip) of the apparatus to be connected. Thus, the connection can be simplified. Furthermore, since a clip as the separate component is not attached to the adhesive electrode, the number of parts can be decreased and the assembly is not bulky.

When the electrode of the present invention is used as an electrode for medical attention, the cut portion rolls up, projecting outwards, and the projected portion can be easily connected to a terminal of the medical or diagnotical equipment. Furthermore, since the force exerted in the direction in which the electrode is peeled off at the time of connection is absorbed by the action that the cut portion rolls up, no peeling force is exerted onto the electrode itself, as a result of which no stress is formed on the skin surface.

The present invention will hereinafter be explained in detail by reference to the drawings.

In FIGS. 1 to 9, the electrode comprises a flexible electrically conductive substrate (1), and an electrically conductive adhesive layer (2) provided on the back of the electrically conductive substrate (1) and a shrinkable layer (3) provided on the top of the electrically conductive substrate (1). In the electrically conductive substrate (1), a non-adhesive area (A) is formed, to which the electrically conductive adhesive layer (2) is not substantially attached.

Figure 2:
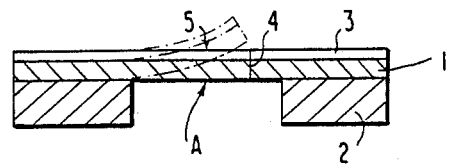
FIG. 2 is a cross-sectional view taken along line II—II in the electrode shown in FIG. 1.
Figure 3:
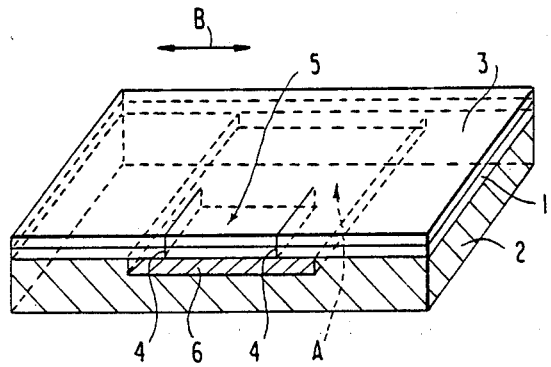
FIG. 3 is a perspective view of another embodiment.

The above non-adhesive area (A) may be formed in the following manners. The area (A) is formed in a rectangular form in the central portion of the electrically conductive substrate (1) except for the electrically conductive adhesive layer (2), as shown in FIGS. 1 and 2. A non-adhesive liner layer (6) is provided between the electrically conductive substrate (1) and the electrically adhesive layer (2) so that the electrically adhesive layer (2) is not substantially bonded to the electrically conductive substrate (1), as shown in FIG. 3. The area (A) is formed in the middle portion of the electrically conductive substrate (1) except for the electrically conductive adhesive layer (2), as shown in FIGS. 4 to 9.

In this case, the electrically conductive substrate (1) is a copper foil having a thickness of 100 μm. The electrically conductive adhesive layer (2) is made of an acryl-based adhesive with silver powder added and mixed. The non-adhesive liner layer (6) is formed by providing a non-adhesive foamed material in a compressed state.

If the non-adhesive liner layer (6) is formed using a foamed material in a compressed state, the repulsion force of the layer (6) makes easier the rolling-up of the cut portion, i.e., the connection terminal portion.

Figure 8:
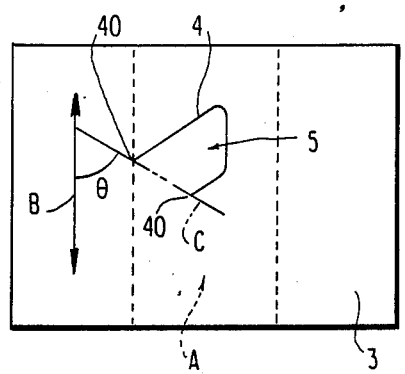

In this case, the above shrinkable layer (3) is made of a heat shrinkable polyvinyl chloride resin. In the shrinkable layer (3) and the electrically conductive substrate (1), the connection terminal portion (5) due to the cut (4) is provided at a position corresponding to the above non-adhesive area (A). As shown in FIG. 8, the connection terminal portion (5) is designed such that the direction (C) of line connecting the base ends (40)(40) of the cut (4) is in an angle of 0° to 60° relative to the direction of shrinkage of the shrinkable layer (3), i.e., the direction of arrow B. Thus, the connection terminal portion (5) rolls up, thereby projecting outwards by the shrinkage of the shrinkable layer (3) (heat shrinkage in this case).

The above connection terminal portion (5) will be explained in more detail below.

Figure 4:
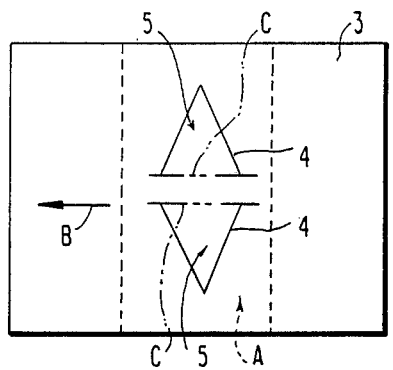
Figure 5:
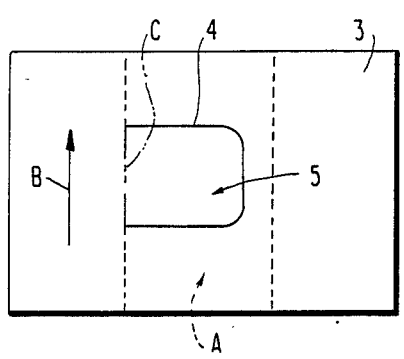
Figure 6:
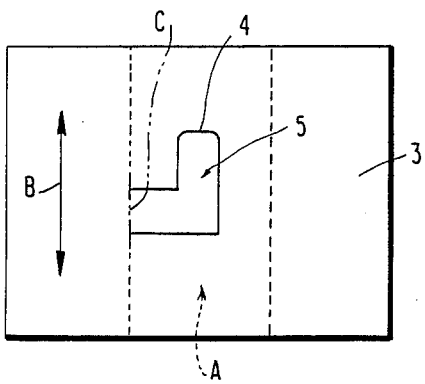
Figure 9:
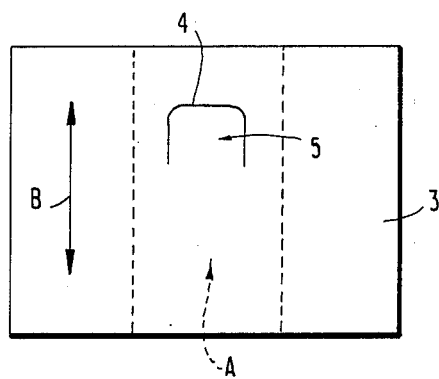

As shown in FIGS. 1 and 2, the connection terminal portion (5) may be formed by cutting both the shrinkable layer (3) and the electrically conductive substrate (1) in the direction of thickness in the U-shaped form at the position corresponding to the non-adhesive area (A). As shown in FIG. 3, at the non-adhesive area (A) formed by providing the non-adhesive liner layer (6) between the electrically conductive substrate (1) and the electrically adhesive layer (2), two lines are formed in parallel with each other with a suitable interval from the end thereof and further in both the electrically conductive substrate (1) and the shrinkable layer (3) in the direction of thickness thereof to thereby form the cut (4). As shown in FIG. 4, two cuts(4) in the V-shaped form may be formed in such a manner that the base ends of the cuts faces each other. As shown in FIG. 5, when the portion is provided by the cut on the nearly center of the non-adhesive area (A), the cut may be formed in such a manner that the base end of the cut (4) is positioned at the edge of the non-adhesive area (A). As shown in FIG. 6, the cut (4) may be formed in the hook form. In all cases, the connection terminal portion (5) is formed such that the angle between the direction of shrinkage (direction of arrow B) of the shrinkable layer (3) and the direction of line connecting end bases of the cut (direction C) is 0°; that is to say, the direction of shrinkage (B) is in parallel with the direction (C) of line connecting the base ends of the cut (4).

Figure 7:
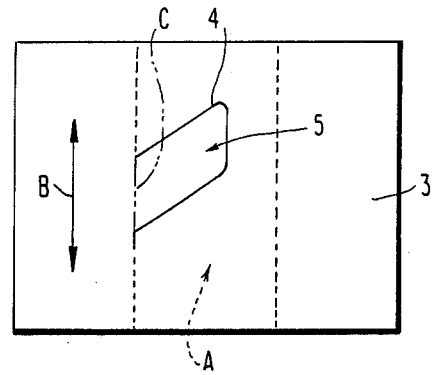

Instead of the above embodiments, the connection terminal portion (5) may be formed as follows. As shown in FIG. 7, the connection terminal portion (5) may be formed such that it is at a slant angle to the direction of shrinkage of the shrinkable layer (3) (direction of arrow B). As shown in FIG. 8, the direction (C) of line connecting the base ends of the cut (4) in the connection terminal portion (5) is at an angle of up to 60° relative to the direction of shrinkage (B) of the shrinkable layer (3), in this case, at an angle of 60°.

In the above embodiments, as the shrinkable layer (3), a heat shrinkable polyvinyl chloride resin is used. In place of the polyvinyl chloride resin, other heat shrinkable layers can be used. Furthermore, in place of the heat-shrinkable layers, shrinkable layers which shrink upon irradiation can be used.

By employing the above construction, a non-shrinkable material can be used for the outer layer without preventing the shrinkage of the shrinkable layer.

Furthermore, as the electrically conductive substrate, other metal foils, metal sheets, or laminated sheets of metal and synthetic resin films (sheets) can be used.

The prevent invention possesses the above structure. As a result, the number of parts is decreased, the number of steps of production is small, the production is simplified, the continuous production is possible, and the productivity is excellent. Further, the present invention has the effect that in electrical connection, the connection of the terminal portion, which is projected by shrinking the cut, to a terminal of the equipment to be connected (equipment) is ensured.

Since the present invention does not have such terminals as clips, hooks and pins, it provides the effects that the electrode is not bulky, so that wrapping, transportation and storage become unexpensive.

In a case where the electrode of the present invention is used as an electrode for medical attention, it is attached to the skin and the connection terminal portion is projected, and the terminal portion is connected to the terminal of the medical or diagonatic equipment. During this process, the connection terminal portion rolls up suitably and no peeling force is applied to the skin surface. Accordingly, no stress is experted to the skin surface and there can be obtained the effect that the electrode can be used in a stable manner for a long time.

While the invention has been described in detail and with reference to specific examples thereof, it will be apparent to one skilled in the art that various changes and modifications can be made therein without departing from the spirit and scope thereof.

What is claimed is:

1. An electrode comprising an electrically conductive substrate and a shrinkable layer laminated on the substrate, wherein a cut is provided through the shrinkable layer and into said substrate and said shrinkable layer is shrunk so as to expose said substrate and form a connection terminal portion projecting outwards.

2. The electrode as claimed in claim 1, wherein said cut begins at a first base and terminates at a second base, wherein said shrinkable layer has one direction upon shrinkage, and wherein the direction of a line connecting the base ends of the cut is at an angle of 0° to 60° to the direction of shrinkage of the shrinkable layer.

3. The electrode as claimed in claim 1, wherein an electrically conductive adhesive layer is provided on the surface of the electrically conductive substrate opposite that of the shrinkable layer, but not on the connection terminal portion.

4. The electrode as claimed in claim 1, wherein the shrinkable layer is at least one member selected from the group consisting of a heat shrinkable layer, a radiation-sensitive hardening type shrinkable layer and a radiation-sensitive cross-linking shrinkable layer.

5. The electrode as claimed in claim 1, wherein the electrically conductive substrate is a laminate of at least one electrically conductive layer selected from the group consisting of a metal deposited layer, a non-electrolytic plated layer and a metal foil layer, and at least one insulator selected from the group consisting of a plastic film, paper, a fabric and an unwoven fabric.

6. The electrode as claimed in claim 1, wherein a non-adhesive liner layer having a smaller area than the substrate is provided on the surface of the electrically conductive substrate opposite that of the shrinkable layer so as to cover the connection terminal portion, and wherein an electrically conductive adhesive layer is provided so as to cover both (i) the remaining exposed surface of the electrically conductive substrate and (ii) the non-adhesive liner layer.

* * * * *